Dec. 1, 1964 H. J. HEIDRICH ET AL Plant Pat. 2,459
PEACH TREE
Filed Aug. 29, 1963
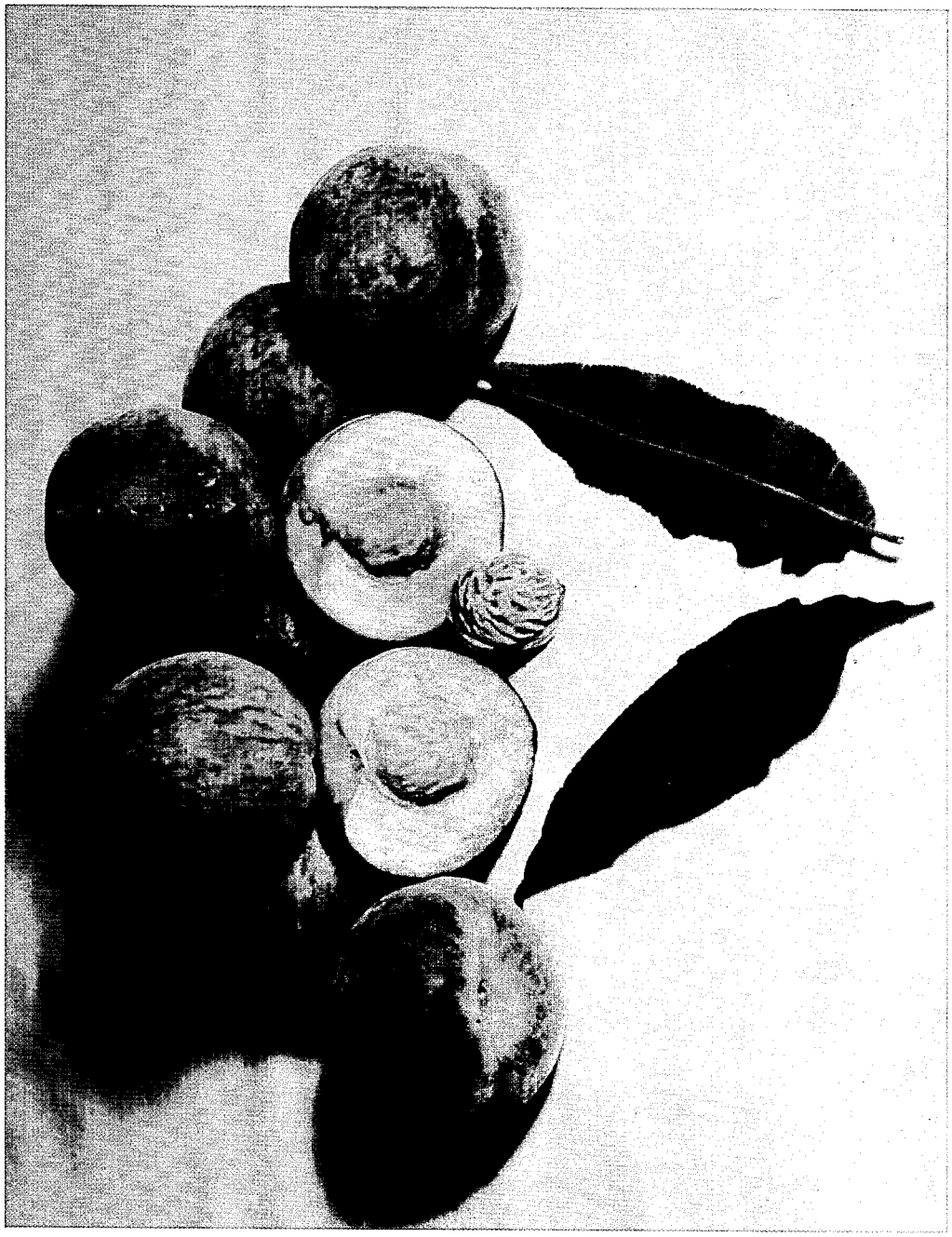
Inventors.
H. J. Heidrich and
C. F. Wiedeman
By: Robb & Robb
Attorneys.

United States Patent Office

Plant Pat. 2,459
Patented Dec. 1, 1964

2,459
PEACH TREE

Herman J. Heidrich, Orlando, Fla., and Charles F. Windham, Davisboro, Ga., assignors to Herman J. Heidrich & Sons, Inc., Orlando, Fla., a corporation of Florida

Filed Aug. 29, 1963, Ser. No. 305,569
1 Claim. (Cl. Plt.—43)

The present invention relates to a new and distinct variety of peach tree which was discovered by us in the cultivated orchard of our assignee at Davisboro, Georgia, as a newly found seedling.

At the time of our initial discovery aforesaid, an orchard of the peach variety, known as "Hiland" (unpatented), was being operated under our care, supervision and control, and in the course of our work, our attention was attracted to a small volunteer seedling, which we estimated to be about two years old, and which we discovered growing amongst the "Hiland" trees in this orchard. Our discovery was made by virtue of the fact that the few peaches borne by the small seedling appeared to be much further advanced toward ripening than the fruit of any of the surrounding trees. Accordingly, steps were taken by us immediately to carefully preserve the seedling and to keep it under close observation, as well as to bud additional trees therefrom.

Continued observations of the original seedlings, as well as the budded trees, convinced us that our newly found seedling was a new and distinct variety, as evidenced by the following unique combination of characteristics which were outstanding therein and which distinguished the same from all varieties then being grown by us or otherwise known to us:

(1) A general resemblance of the tree to trees of the variety known as "Hiley" peach (unpatented);

(2) An unusual and very early fruit ripening habit, with the picking dates ranging from the last week of April to the first week of May at Davisboro, Georgia; and (3) Attractive fruit of good quality and high color, resembling the variety known as "Early Rose" peach (unpatented).

Asexual reproduction of our new variety by budding, as performed by us at Davisboro, Georgia, shows that the foregoing characteristics and distinctions come true to form and are established and transmitted through succeeding propagations.

The accompanying drawing shows typical specimens of the foliage, fruit and stone of our new variety, as depicted in color as nearly true as it is reasonably possible to make the same in a color illustration of this character, said fruit being shown in elevation and also in cross-section, with the half-sections exposing the cavities and the stone being shown separately, and the foliage specimens depicting both the upper and under surfaces of typical leaves.

The following is a detailed description of the new variety, with color terminology in accordance with Koster's Color Guide, except where general color terms of ordinary dictionary significance are obvious:

Locality where grown and observed: Davisboro, Georgia.
Dates of first and last pickings: April 30 and May 7, respectively.
Tree: Medium size; vigorous; spreading; open; vase-formed; hardy; productive; regular bearer.
- *Trunk.*—Stocky; smooth.
- *Branches.*—Medium stockiness; smooth. Color—brown. Lenticels—numerous; small.
- *Leaves.*—Medium size; lanceolate; acutely pointed; medium thickness; smooth. Lenth—about 6½ inches. Width—about 1⅛ inches. Color:—upper surface—near Taxus Green, Plate No. 81; under surface—near Cedar Green, Plate No. 80. Margin—crenate; finely serrate. Petiole—medium length (about ⅜ inch); medium thickness. Glands—average about 7 in number; alternate; small; reniform; color—green. Stipules—occasionally 2.

Flower buds: Hardy; large, short; pointed; appressed; medium pubescence.
Flower:
- *Dates of first and full bloom.*—February 20 and February 28, respectively; early.
- *Size.*—Medium.
- *Color.*—Pink.

Fruit:
- *Maturity when described.*—Picking ripe.
- *Size.*—Variable; average about 2 inches in diameter.
- *Form.*—Uniform; globose; oblate.
- *Stem.*—Medium length (about ⅜ inch); slight adherence to stone; medium pubescence.
- *Skin.*—Medium thickness; tenacious to flesh; no tendency to crack during wet or dry seasons. Color—high red (blotched near Amaranth Red, Plate No. 43, with faint blush of Solferino Red, Plate 40, overlying a ground color of Cream Yellow, Plate 4), and comparable to the color of the fruit of "Early Rose" peach. Down—short.
- *Flesh.*—Color—Cream Yellow, Plate 4, mottled with French Purple, Plate 42 near the skin, and with pit cavity color near Sulphury White, Plate 3.
- *Amygdalin.*—Moderate.
- *Juice.*—Abundant.
- *Texture.*—Firm.
- *Fibres.*—Few.
- *Ripens.*—Even.
- *Flavor.*—Mild.
- *Aroma.*—Wanting.
- *Eating quality.*—Good.

Stone: Cling.
- *Size.*—Length—about 1 inch. Breadth—about ¾ inch. Thickness—about ⅝ inch.
- *Form.*—Oval.
- *Base.*—Oblique.
- *Hilum.*—Narrow.
- *Apex.*—Acuminate.
- *Sides.*—Equal; curved on right and left sides.
- *Surface.*—Regularly furrowed throughout.
- *Ridges.*—Ridged throughout; rounded toward base.
- *Pits.*—Pitted throughout.
- *Ventral edge.*—Elongated; thick; with wing toward base.
- *Dorsal edge.*—Narrow; with deep grooves throughout.
- *Color.*—Near white, with light scattering of brown.
- *Tendency to split.*—Slight in wet season.

Use: Market.
Keeping quality: Good.
Shipping quality: Good.

We claim:

A new and distinct variety of peach tree of the yellow-fleshed clingstone fruit-bearing class, substantially as shown and described herein, characterized as to novelty by the unique combination of a general resemblance of the tree to trees of the variety known as "Hiley" peach (unpatented), an unusually very early fruit ripening habit, with the picking dates ranging from the last week of April to the first week of May in the State of Georgia, and the production of attractive fruit of good quality and high color resembling the variety known as "Early Rose" peach (unpatented).

No references cited.

ABRAHAM G. STONE, *Primary Examiner.*